United States Patent [19]

Crooks et al.

[11] Patent Number: 4,541,716
[45] Date of Patent: Sep. 17, 1985

[54] DETECTION OF DEFECTS IN A CIRCULAR OR SPIRAL DIFFRACTION GRATING

[75] Inventors: Horatio N. Crooks; Martin J. Kelly, Jr., both of Indianapolis, Ind.

[73] Assignee: RCA Corporation, Princeton, N.J.

[21] Appl. No.: 485,474

[22] Filed: Apr. 15, 1983

[51] Int. Cl.$^4$ ............................................. G01N 21/00
[52] U.S. Cl. ..................................... 356/237; 356/354
[58] Field of Search ............... 356/237, 354, 355, 359, 356/321; 250/562, 572; 358/106

[56] References Cited

U.S. PATENT DOCUMENTS

| | | | |
|---|---|---|---|
| 3,460,841 | 8/1969 | Caldwell | 274/42 |
| 3,915,526 | 10/1975 | Taylor | 356/354 X |
| 4,030,835 | 6/1977 | Firester et al. | 356/111 |
| 4,300,143 | 11/1981 | Bell et al. | 346/135.1 |
| 4,352,564 | 10/1982 | Roach | 356/237 X |
| 4,395,122 | 7/1983 | Southgate et al. | 356/237 |

OTHER PUBLICATIONS

"Technology Focus: Video Discs-a Triquetral Marketplace," Electronic Engineering, Sep. 1980, p. 129, et seq.

Primary Examiner—Davis L. Willis
Assistant Examiner—Matthew W. Koren
Attorney, Agent, or Firm—Birgit E. Morris; Donald S. Cohen; Joseph D. Lazar

[57] ABSTRACT

Topographical defect detecting apparatus and process for optically inspecting a circular or spiral track surface defining a diffraction grating such as exists on a video disc or optical disc record. Light from a substantially point source illuminates the track surface. Diffracted reflections from the surface are viewed by the human eye with or without the aid of a TV camera and monitor.

Non-uniformities in track spacing and deviation from average surface flatness are readily observable.

8 Claims, 13 Drawing Figures

DETECTION OF DEFECTS IN A CIRCULAR OR SPIRAL DIFFRACTION GRATING

The present invention relates to optical inspection apparatus for detecting defects in the topography of a circularly or spirally tracked information record. More particularly, the invention relates to viewing defects in a record, such as a video disc of the type described in U.S. Pat. No. 3,842,194 issued to J. K. Clemens.

The defect detection principles of the present invention are applicabe to optical inspection of surfaces containing closely and uniformly spaced spiral or circular tracks such as exist on, for example, video disc and optical disc records at various stages throughout the record mastering and replicating processes.

BACKGROUND OF THE INVENTION

The Clemens patent discloses a video disc for use with a playback system of the variable capacitance type. In one configuration of the Clemens' system, information representative of recorded picture and sound is encoded in the form of a relief pattern in a relatively fine spiral groove on the surface of a disc record. For example, groove widths of approximately 2.6 micrometers and groove depths of about 0.5 micrometers may be used. During playback, capacitive variations between a conductive electrode on a stylus and a conductive property of the disc record are sensed to recover the prerecorded information.

In accordance with the Clemens' format, the video information may be recorded as relatively short (e.g., 0.6–1.6 micrometers) relief variations along the length of the spiral groove. Illustratively, the method of recording may be of a type shown in U.S. Pat. No. 4,044,379 to J. B. Halter. Pursuant to the Halter method, an electromechanically-driven stylus (e.g., of diamond) having a trangular shape, responsive to a combined video and audio signal, records relatively short geometric variations, representative of the time variations of the signal, on a surface of a metal substrate. After the electromechanical recording operation, the recorded surface of the metal substrate has a relief pattern corresponding to that which is desired in the final record. In the replicating process, masters are made from the substrate. Molds are then made from the masters and stampers are made from the molds. The stampers are used in the process of pressing a vinyl record having the desired relief pattern.

During each of the above-identified record manufacturing processes, various kinds of defects can develop which may affect the record groove quality and which are difficult to detect in view of the fineness of the groove structure typically employed in a video disc (e.g., 10,000 groove convolutions per inch [4000 convolutions per cm]).

Because of the very small dimensions of the signals recorded on the video disc, very small defects can disturb the playback of a disc. Many defects which cause trouble in playback are difficult to see when viewed under normal lighting or when observed through a microscope.

Defect detection systems utilizing collimated (laser) light beams to illuminate grooved surfaces are described in U.S. Pat. No. 4,030,835 issued to A. H. Firester et al. on June 21, 1977; copending U.S application Ser. No. 258,759, filed Apr. 29, 1981 by Southgate et al now U.S. Pat. No. 4,395,122; and copending U.S. patent application Ser. No. 155,989, filed May 30, 1980 by W. R. Roach now U.S. Pat. No. 4,352,564. These systems utilize certain diffraction orders reflected from the incident collimated light to identify defects of various kinds. U.S. Pat. No. 3,460,841, issued to K. G. Caldwell on Aug. 12, 1969, describes a system for testing a grooved record utilizing a point source of non-collimated light to illuminate the grooved record surface to effect diffracted reflections. The diffracted reflections are viewed to identify damage to the grooves.

None of the above described systems for inspecting grooved surfaces are useful for inspection purposes to identify quickly and easily defects in the topography of grooved surfaces defining a diffraction grating.

Moreover, optical discs having closely spaced spiral or circular information tracks formed of pits or bumps in the surface also form diffraction gratings and also may have defects in the topography that are not quickly and easily identified. U.S. Pat. No. 4,300,143 by A. E. Bell et al., describes an optical disc with the associated laser recording and playback apparatus. See also "Technology Focus: Video discs—a triquetral marketplace," *Electronic Engineering*, Sept. 1980, pp. 129, et seq.

SUMMARY OF THE INVENTION

According to the present invention, defects in the topography of a surface having a spiral or circular diffraction grating are detected by utilizing a point source of polychromatic light positioned on an axis normal to the surface to illuminate the surface. Reflections of essentially the fourth through seventh diffraction orders are optically sensed at a position on the axis above the light source.

According to one aspect of the invention, the entire disc is illuminated and a sensor such as a TV camera is oriented to view the entire disc and present a picture on a TV monitor.

In another aspect of the invention, a portion or sector of a disc record is incrementally sequentially rotated about the central axis of the disc in order to inspect the entire surface in steps. A sensor, such as a TV camera, is oriented to view a preselected portion or sector of the disc and present a picture on a TV monitor.

The disc may have spiral information track convolutions in the form of a groove or a series of pits or bumps in the surface. Either form of disc defines diffraction grating defects which can be detected.

DETAILED DESCRIPTION OF THE PREFERRED EMBODIMENT

The present invention utilizes the principle of a diffraction pattern resulting from the illumination of the close and regular spacing of grooves, for example, of a video disc. When light impinges on the disc at appropriate angles to cause the diffracted light to strike a sensor such as an eye, the eye will see the disc in a multitude of colors. In addition, the eye will see imperfections in the disc surface which are greatly enhanced relative to what is seen under ordinary lighting conditions. Under appropriate lighting and viewing conditions, the entire recorded area of one surface of a video disc can be viewed by diffracted light and defects over the entire surface can be detected. This phenomenon exists when both the illuminating light source and the eye are positioned on an axis perpendicular to the disc surface and intersecting the disc at the center of the circular or spiral groove pattern, as seen in FIG. 1 illustrating one embodiment of the invention.

Figure 1:
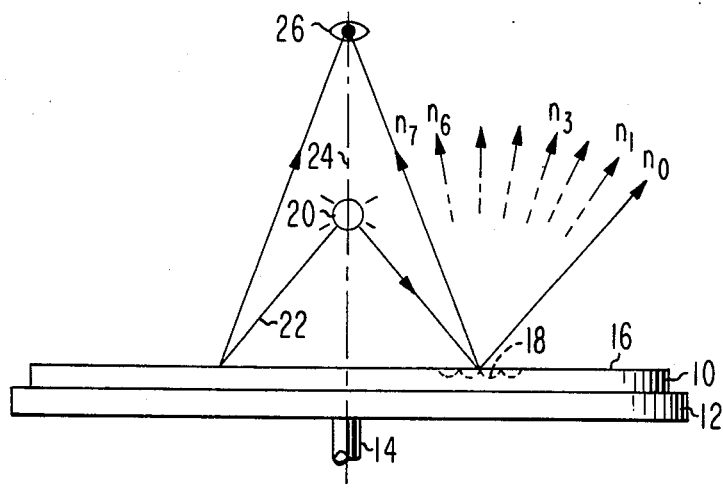
FIG. 1 is a schematic in side elevation of an illuminated grooved disc for the purpose of developing diffraction patterns according to the principles of the present inventions.

FIG. 1 shows a video disc 10 rotatively supported on a turn table 12 of a player driven by a shaft 14. The surface 16 of the disc is provided with spiral grooves 18 which are illuminated by a point source 20 of light. The light source 20 is preferably polychromatic light in the visible spectrum providing illumination rays 22 to illuminate the entire surface 16. The light source 20 is positioned above the surface 16 on the center axis 24, which is perpendicular to the surface. Above the position of the light source 20 the viewer's eye 26 is positioned to view the entire surface 16 at a height sufficient to achieve the desired field of view. Light is reflected from the grooves 18 according to known optical principles comprising the zero order (specular) reflection $n_0$ and the diffracted reflections $n_1 \ldots n_7$. It will be noticed that the lower the diffraction number (n) the more the light is reflected away from the central axis 24 and the higher the number the more is reflected towards the central axis 24.

Figure 2:
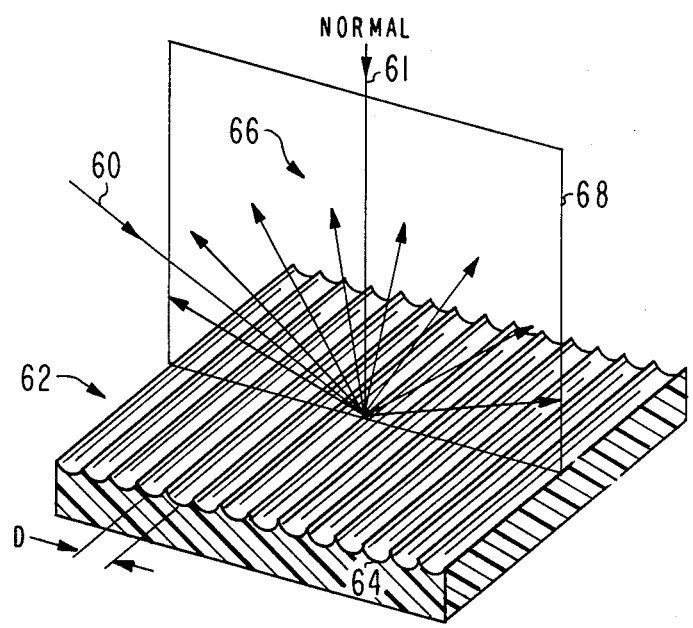
FIGS. 2, 3, 4 and 5 are schematics illustrating the geometry of the optics involved in the present invention.

The diffraction principles involved in the present invention will be explained by reference to FIGS. 2–5. As known in the optical art, when a light beam 60 is directed at a surface 62 which contains equally-spaced (D) grooves 64 and, in particular, when the direction of the light beam 61 is perpendicular to the grooves 64, the light is reflected (diffracted) into a plurality of beams 66 lying on the plane 68 defined by the incoming light beam 60 and the normal 61 to the surface 62 as shown in FIG. 2. The reason for the multiple reflection directions is that in each of these directions, light waves from adjacent grooves combine in phase, as will be explained, to produce multiple peaks in the light intensity.

Figure 3:
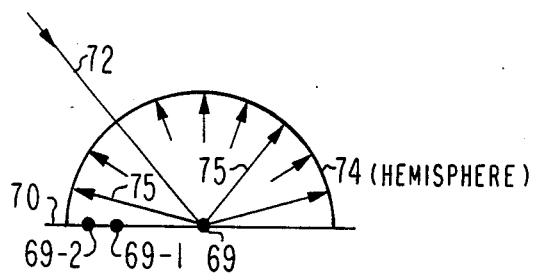

According to Huygens' principle, each point 69 on a surface 70 which is illuminated by a beam of light 72 reflects light uniformly in all directions 74 as indicated in FIG. 3. The phase of the reflected light waves 75 is related to the phase of the incident light waves 72 in the same way at all points 69-1, 69-2, etc., in the surface 70, i.e., if two points (69-1 and 69-2) are illuminated in phase with each other, the reflected light is also in phase.

Although light from each illuminated point is considered to be reflected uniformly throughout the entire hemisphere 74 surrounding the point 69, when the light is reflected from a number of points, the light is not uniform but rather is reflected in preferred directions.

The amount of light reflected in a given direction is measured by the energy that would be received by a photodetector positioned along a line in that direction. The energy received depends upon the amplitude of the electric vector in the light wave. When light from several sources impinges on the detector at the same time, the detector responds to the vector sum of all the light waves involved. If all the light waves are in phase, a large vector sum results and one would say that there is a relatively high light level in that direction. If the light waves are such that the vector sum is nearly zero, then one would say that there is very low light level in that direction.

Figure 4:
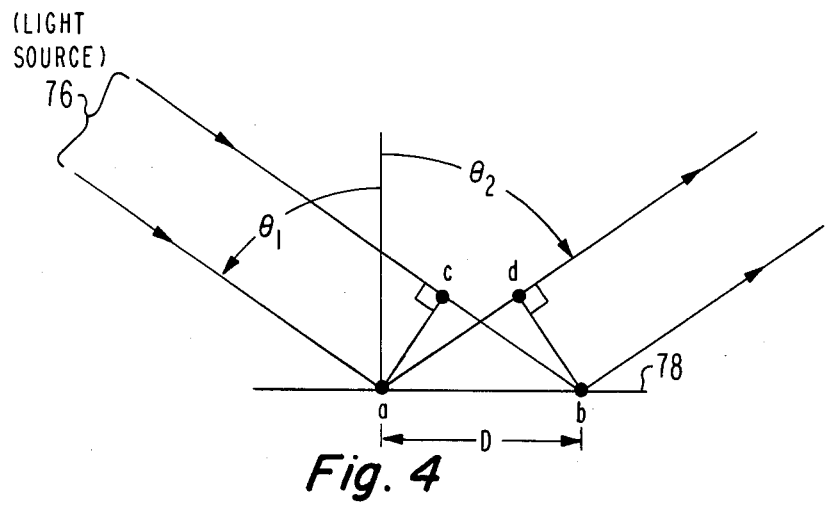

Now, consider the situation of two reflecting points as shown in FIG. 4. Light from the source 76 arrives at points a and c in phase. Light from point a is reflected to some point d and light from c continues to the surface 78 at point b where it is reflected. If the distance from a to d is equal to the distance from c to b, then light reflected from surface points a and b in a direction perpendicular to the line d-b will be in phase and will exhibit a light intensity peak in this direction. If distance a-d is increased or decreased by an integral number of light wavelengths, this is still true and establishes other directions for which there are light intensity peaks. Thus, it is seen that light is reflected preferentially in those directions $\theta_2$ for which the following equations are true:

$$|cb - ad| = n\lambda \tag{1}$$

$$|D \sin \theta_1 - D \sin \theta_2| = n\lambda \tag{2}$$

$$|\sin \theta_1 - \sin \theta_2| = n\lambda/D \tag{3}$$

$$\sin \theta_2 = \sin \theta_1 \pm n\lambda/D \tag{4}$$

where D is the distance between the two points a and b; $\lambda$ is the wavelength of the light; and n is an integer.

Equation (4) defines the reflection directions for all pairs of reflecting points (a,b) in the surface 78. When the distance D between the points is different for each pair, the only way equation (4) can be satisfied for all pairs at the same time is for n=0 and $\theta_1 = \theta_2$. This is the condition conventionally called "specular reflection."

When reflecting points can be matched in pairs, all with the same distance D, the condition is quite different. Now, the equation can be satisfied by a plurality of values of $\theta_2$ where:

$$\theta_2 = \sin^{-1}(\sin \theta_1 \pm n\lambda/D) \tag{5}$$

where $(\sin \theta_1 \pm n\lambda/D)$ varies only between $-1$ and $+1$. An illustration of the application of equation (5) to an embodiment of the invention will be described hereinafter.

When a surface contains equally spaced grooves of similar cross sections, any point on one groove can be paired with a similar point on an adjacent groove at a distance D from the first point, where D is the groove-to-groove spacing. This results in the condition illustrated in FIG. 2, wherein an incident light beam is reflected into a plurality of directions 66. As known in the art of optics, the value n in equation (5) is the "order" of the diffracted ray. Specular reflection is that for which n=0.

If the light is not monochromatic, it contains energy at various wavelengths. Each different wavelength gives a different angle of diffraction for all orders except for n=0. Thus, instead of having the light diffracted in sharply defined directions, it is spread out over some angle about each of the directions calculated for the predominant wavelength of the light. Because of this, the diffraction pattern will contain energy peaks and valleys as a function of angle $\theta_2$. If one were to position his eye in one of these peaks and look at a grooved surface, he would see the grooved surface (62, FIG. 2) in color because each of the different wavelengths is diffracted to his eye in a different direction and from a different part of the surface.

If we now postulate that the light source (20, FIG. 1) be positioned on the axis 24 of a grooved disc 16 at some distance from the disc surface 18, it should be clear that, because of circular symmetry, the light strikes all azimuthal positions with the same radius at the same angle relative to the normal to the surface. If we also position the eye 26 on the axis 24 of the disc 10 at some distance from the surface, it will also view all azimuthal positions with the same radius at the same angle. Thus, we have a situation where the eye 26 can view all azimuthal positions of the disc under the same conditions at the same time. If the eye 26 is positioned at one of the diffraction pattern peaks, a large part of or perhaps the whole surface of the disc can be viewed at one time.

The essence of the present invention is that the above-stated conditions are met. Thus, the polychromatic light source is positioned along an axis perpendicular to the disc surface having the diffraction grating. The light impinging on the surface will provide a pattern of reflections that can be optically sensed by the eye by being properly positioned along the axis on which the light source is positioned. The intensity of the light reflected from any portion of the disc to the eye is critically dependent upon the uniformity of (1) the groove spacing and (2) the average surface flatness. The groove spacing is defined by D in equation (5) while the average surface flatness is manifested by a uniform angle of incidence angle $\theta_2$. If either of these parameters (1) and (2) are not uniform, the discrepancy is very obvious by the fact that the reflected light intensity is different in that portion from the average reflected light intensity. The observed effect is similar to that when a supposedly smooth surface is illuminated at an oblique angle and looked at from the direction of specular reflection.

Although the invention described herein provides an observed effect similar to that when viewing a surface with oblique light and specular reflection, it overcomes some problems that are experienced with the specular viewing methods. These problems are: (1) only a small area of the disc can be viewed at one time if the light source is small, (2) if the light source is large and not collimated (as from a diffuse source) any one point of the disc is viewed not only by specular reflection with the light from one small part of the source, but also by diffuse reflection with light from all other parts of the light source, a condition which reduces the variation in brightness which one is trying to detect, (3) because of the oblique viewing angle, defects subtend a smaller angle to the eye and thus can be seen only with poorer resolution; and (4) because of the oblique viewing angle, greater depth of focus is required in any sensor such as a TV camera which may be used to observe the disc surface.

The present invention enables one to easily look either at the entire disc surface, or a considerable fraction of the disc surface, with a small light source and an easily focused sensor (e.g., a TV camera) while at the same time preserving the sensitivity of specular reflection so far as surface non-uniformities are concerned. In addition, the present invention provides a picture showing defect in groove spacing uniformity.

Figure 5:
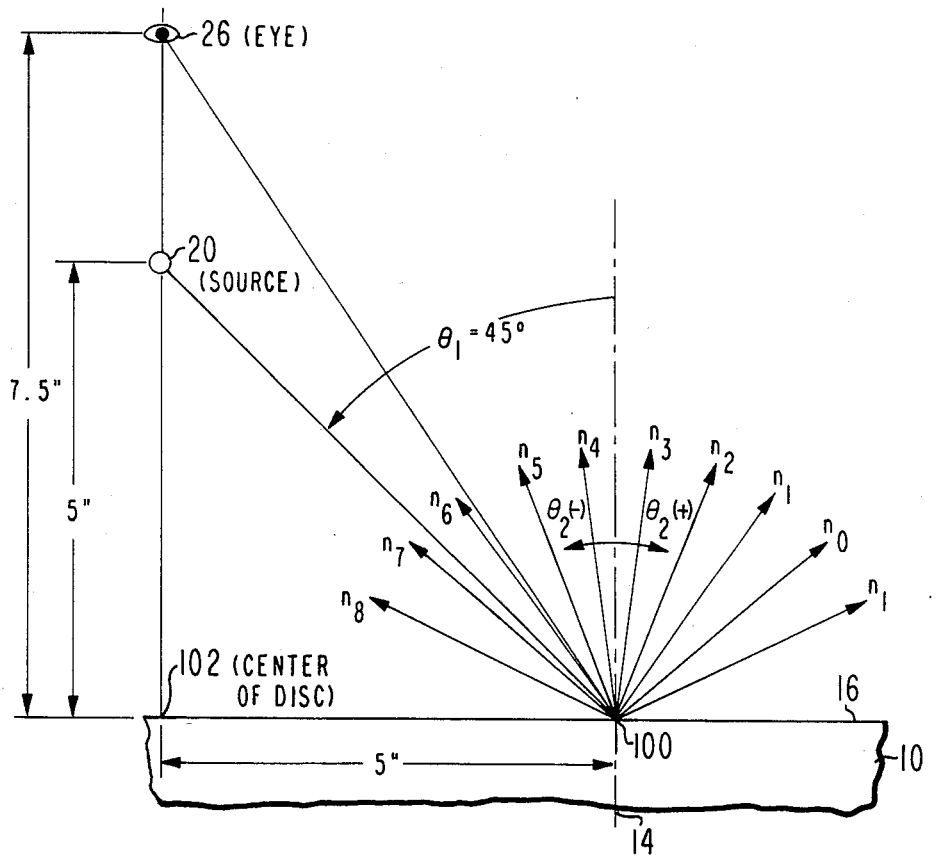

Reference is now made to FIG. 5 which shows additional details of the diffraction process wherein the center of the grooved area of the disc 10 has a radius of 5 inches (12.7 cm), the light source 20 is positioned 5 inches above the surface 16 on the disc axis 14, and the eye 26 is positioned 7.5 inches (19.05 cm) above the disc surface 16 on the axis 24. Under these conditions $\theta_1$ is 45°. The value of $\theta_2$ for each of the diffracted rays can be calculated with equation (5) described above.

Substituting the following variables in equation (5) (repeated here for convenience) results in the following tabulated values of $\theta_2$ (−) and (+) as shown in FIG. 5:

$$\theta_2 = \sin^{-1}(\sin\theta_1 \pm n\lambda/D) \quad (5)$$

wherein $\theta_1 = 45°$; $\lambda = 550$ nm (green light); $D = 2.6$ μm (video disc standard); and n = various integers 0 to 8.

| TABLE OF CALCULATED DIFFRACTION ORDER ANGLES | | |
|---|---|---|
| n | $\theta_2$ (−) | $\theta_2$ (+) |
| 0 | 45.00 | 45.00 |
| 1 | 29.80 | 66.49 |
| 2 | 16.68 | — |
| 3 | 4.42 | — |
| 4 | −7.64 | — |
| 5 | −20.30 | — |
| 6 | −33.87 | — |
| 7 | −49.73 | — |
| 8 | −79.65 | — |
| 9 | — | — |

Only the first diffractive order is developed for $\theta_2$ (+) as seen in FIG. 5 because the illuminating light is at a 45° angle $\theta_1$. Moreover, order 9 for the reflection angle $\theta_2$ (−) does not exist. Different diffraction orders will be reflected for the different variable values defined by equation (5). According to the parameters used in FIG. 5, the eye 26 should see a diffraction maximum completely around the disc 10.

As the viewing position (26) and viewing angle are changed, the diffraction reflection pattern will change. As seen in FIG. 5, the point 100 is 5" from the center 102 of the disc. Point 100 is approximately in the center of the grooved portion formed within 2.5" radial arc. Essentially, the fourth through seventh diffraction order reflections comprise the viewing pattern showing defects. Many experiments have been performed wherein the observations indicating diffraction maxima are observed readily. Defects in parts of the discs were found to present a diffraction pattern that was abnormal from that seen in a reference or calibration disc known to be without imperfections.

The problems in utilizing the arrangment in which the eye of the inspector is used to observe defects in a video disc diffraction pattern make it difficult to use in practice. It is obvious that only one eye of one viewer can view the disc 10 at a given time. Moreover, a slight change in the critical position of the eye can render the system ineffective to view imperfections or defects in the surface, the defects being manifested by aberations or topographical changes in the groove pattern. The use of a television camera provides a means to solve both the problem of a single eye and also to provide a means to position accurately the sensor of the reflected light. Thus, many people can observe the output of a camera serving as the reflection sensor by observing a T.V. monitor. The apparatus of a T.V. camera can be rigidly mounted relative to the disc 10 and the light source 20.

Figure 6:
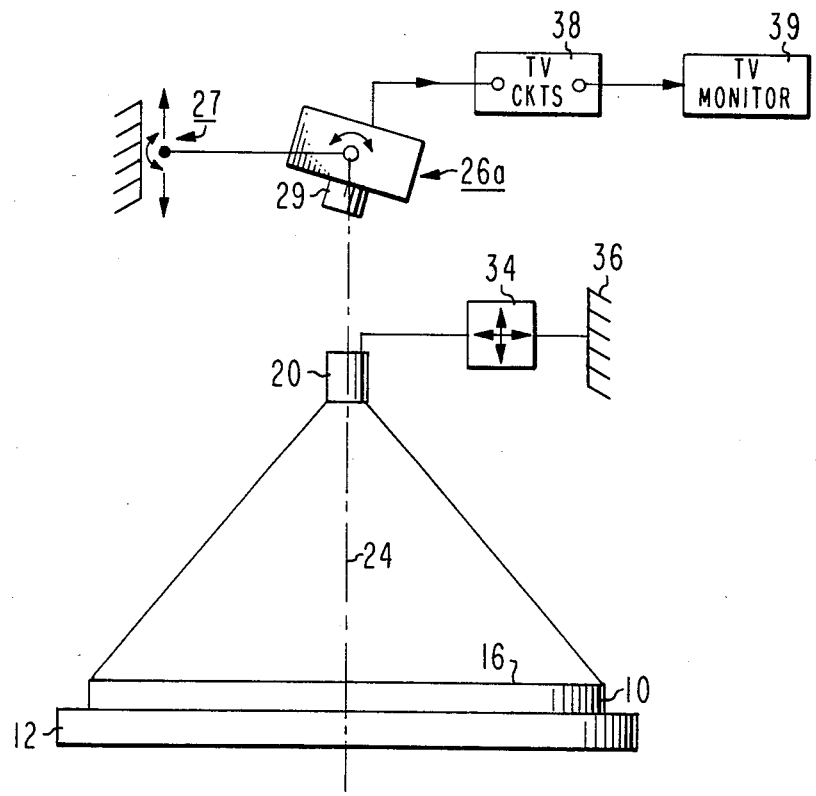
FIG. 6 is a block schematic of a preferred embodiment of the present invention.

FIG. 6 illustrates a prefered form of the invention utilizing a T.V. monitor. As shown in FIG. 6, the light source 20 may be a lamp having a physically small incandescent filament, as, for example, provided in a Tensor-type desk lamp, an incandescent lamp of the type used for automobile head lights, e.g. General Electric No. 1493, or, other similar light sources providing polychromatic light in the visible ranges from a small filament. The light source 20 is positioned on the central axis 24 such that the entire surface 16 is illuminated. Accordingly, a positioning mechanism 34 is provided for moving the light source 20 in any direction relative to a fixed position 36.

A T.V. camera 26a with a lens 29 is positioned with the optical center of the lens 29 on the axis 24 and is provided with adjustable means 27 for rotating the angular position of the camera so that lens 29 can be oriented to any elevation and angular position for viewing the surface 16. Thus, adjustable means 27 is provided both with rotation means and lifting means to locate the camera in any desired position and orientation. The output of the camera 26a is coupled to a conventional T.V. circuit 38 which, in turn, provides a signal for a monitor 39 for displaying that which is seen by the camera 26a.

The position of light source 20 and the position of the camera 26a are such as to provide a reflection pattern that will allow for rapid inspection of a disc 10 that is positioned on table 12. In the more general application of the invention, the entire surface 16 of a disc 10 may be illuminated with a light 20 and a TV camera 26a having a suitable lens 29 positioned to view the entire surface 16 subject, however, to the portion that is masked by the light source 20. In this regard, the central portion of the video disc is not provided with grooves. In practice only a sector of the disc is viewed. A suitable camera 26 used for sector viewing is a 1-inch vidicon type camera having a 50 millimeter, F/6 lens. Because of better resolution, black-and-white television is preferred over color television.

Reference is now made to the photographs made from the display of the T.V. monitor 40 for several video disc records that were inspected in the practice of the invention and which manifested defects in the topography of the groove pattern. Analysis of the particular records were made by other techniques, such as optical microscopy and scanning electron microscopy, and an analysis of the electronic properties and playback characteristics effected by the use of the particular record in operation in a video disc player.

Figure 7A:
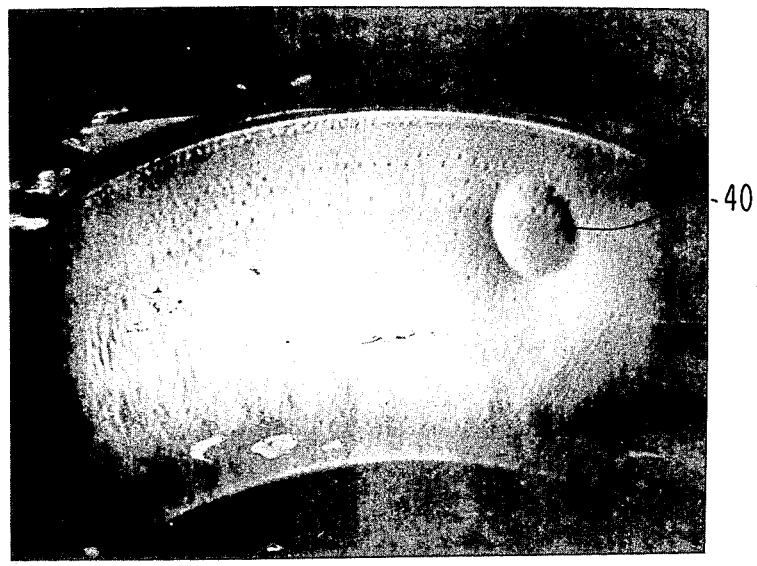
FIGS. 7a, 7b, 8, 9 and 10 are photographs of the TV monitor showing the surface of a video disc illustrating the visual appearance of the illuminated disc manifesting diffraction patterns corresponding to different types of topographical defects.
Figure 7B:
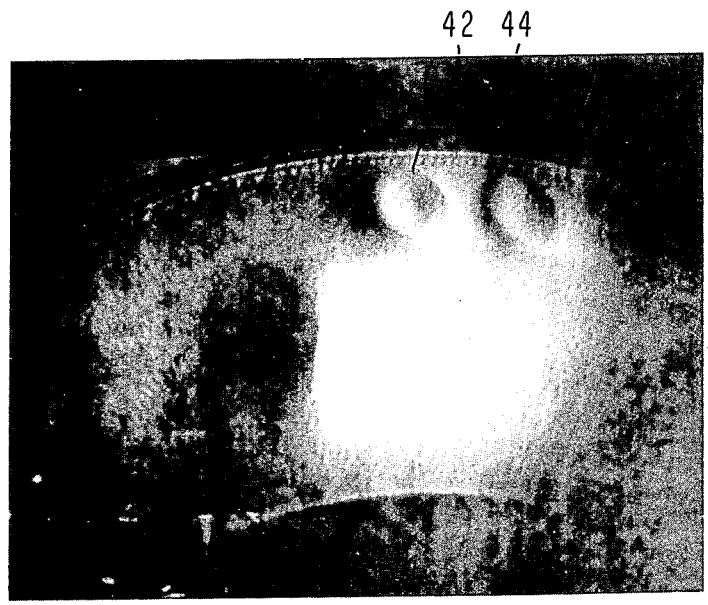

FIG. 7a illustrates a detected defect in the form of a dent 40 encirled as indicated. FIG. 7b shows a different record but with two dents 42 and 44.

Figure 8:
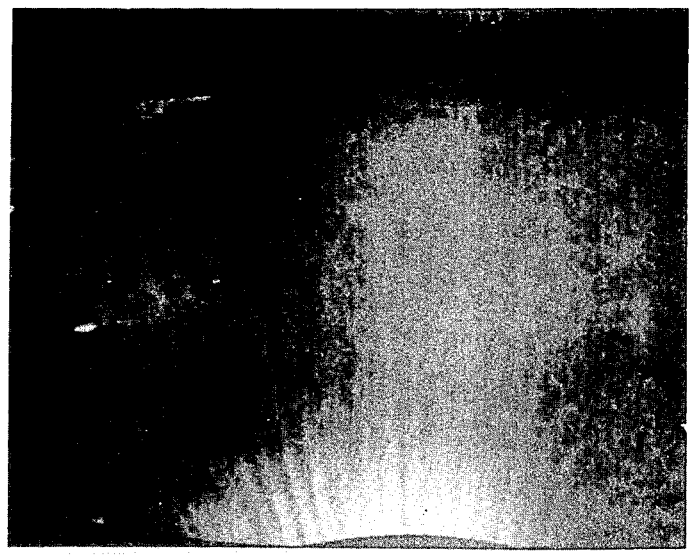

FIG. 8 shows what are termed "spoke marks" that are manifesting stress lines in the process of manufacturing the disc. It is believed these stress lines were caused by nonlinear cooling following the video disc pressing step. These stress lines are believed to be defects in the topography of the grooves that manifest themselves in excessive time base jitter in the playback of the disc. The spoke marks could be the result of discrepancy in the groove spacing. However, we have not investigated this aspect of the apparent defect.

Figure 9:
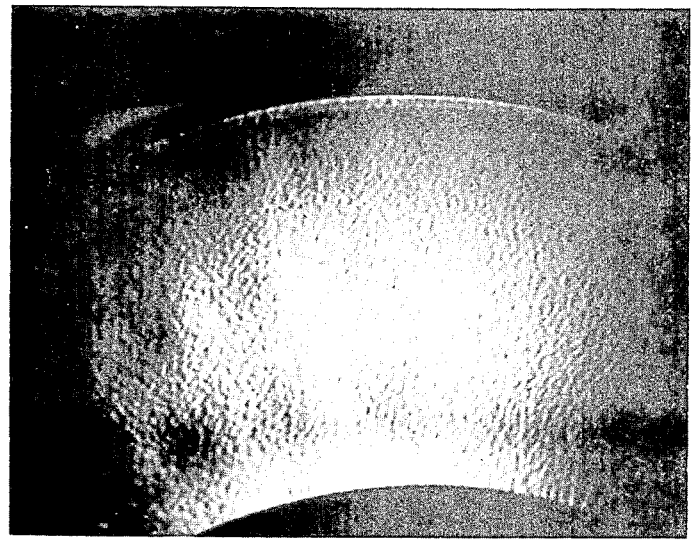

FIG. 9 illustrates what is termed the "orange peel." The topography of the grooves that have this "orange peel" characteristic may cause mistracking of the stylus during playback of the disc which can result in groove skipping and either omissions or repeat plays of affected parts of the disc.

Figure 10:
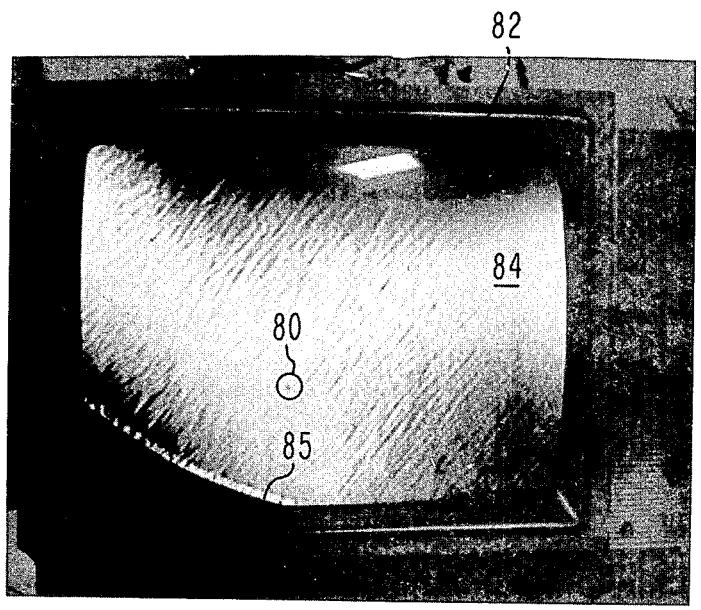

FIG. 10 shows a portion of a disc viewed on a TV monitor in which defects manifested as striations are clearly seen. The portion of the disc that is viewed includes a band of grooves on a 2.7 inch radius of a disc which is six inches in radius. The boundary lines 82 and 85 define the region between which the grooves exist. The grooves are in the portion 84 which includes the defects of striations. The encircled dot 80 is a defect not in the disc but rather in the TV camera. The striations are due to a pattern in the surface of the press mold which mates with the conventional stamper. When the stamper was used on another press mold, the striation marks were not present. This indicated that the press mold contained the defective striations. This was confirmed by microscopic analysis.

Figure 11:
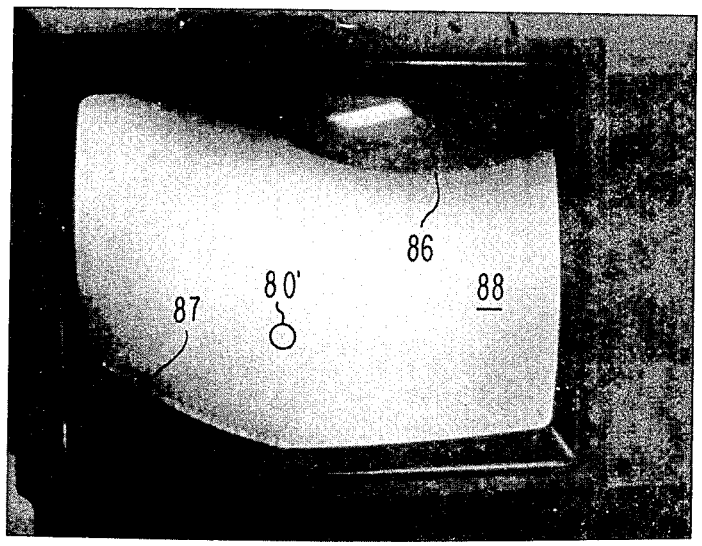
FIG. 11 is a TV photograph of typically "good" grooved "video" disc.

FIG. 11 is a photograph of a TV display showing a typical disc that is free of defects that would otherwise affect the playback properties of the disc. The inner margin 86 and the outer margin 87 are defined, as above, as the limits of the grooved diffraction pattern 88. The defect 80', as shown encircled, is the same defect of the camera as explained with respect to FIG. 10.

Figure 12:
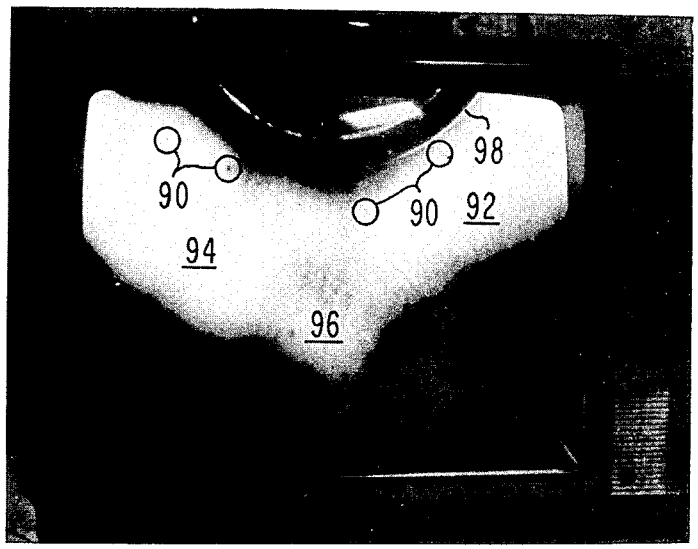
FIG. 12 is a TV photograph of an "optical" disc in which the spiral track consists of a series of information pits in the surface.

FIG. 12 is a TV photograph of an optical disc made by the Discovision Company. This disc is of the type as described hereinabove that provides spiral signal tracks of pits manifesting the signal information. The encircled defects 90 are pinpoint defects in the surface of the disc. The regions 92 and 94 are light whereas region 96 is dark. The general warping of the disc is manifested by the light and light areas 92 and 94 as compared to the dark area 96. The inner region 98 defining the region between no track recordings and the recorded track regions 92 and 94 are as indicated.

What is claimed is:

1. A method for detecting defects in the topography of a surface of a circular record having a circular or spiral diffraction grating having a center comprising the steps of:

positioning a substantially point source of polychromatic light along a preselected axis perpendicular to said surface through said center;

illuminating at least a sector of the surface containing said grating with light from said source;

optically sensing at a predetermined position substantially along said preselected axis, reflections of diffracted light from said sector of said surface;

incrementally rotating said record from sector to sector to sequentially sense the reflected diffraction pattern from the entire disc; and adjusting the respective illuminating and sensing positions to provide a pattern of diffraction reflections manifesting non-uniform spacing or average surface flatness in said diffraction pattern, wherein defects in the topography appear as non-uniformities in the diffraction reflections.

2. The method of claim 1 wherein said diffraction grating is on a disc having a center of rotation at said grating center and said selected axis passes through said center, further comprising the step of positioning said light source along said axis and sensing said reflections at a position along said axis above said source.

3. Apparatus for detecting defects in the topography of a surface of a circular record having a circular or spiral diffraction grating having a center comprising:

means for positioning a substantially point source of polychromatic light along a preselected axis perpendicular to said surface through said center;

means for illuminating at least a sector of the surface containing said grating with light from said source;

means for optically sensing, at a predetermined position substantially along said preselected axis, reflections of diffracted light from said sector of said surface;

means for incrementally rotating said record from sector to sector to sequentially sense the reflected diffraction pattern from the entire disc; and means for adjusting the respective illuminating and sensing positions to provide a pattern of diffraction reflections manifesting non-uniform spacing or average spacing flatness in said diffraction pattern, wherein defects in the topography appear as non-uniformities in the diffraction reflections.

4. The apparatus of claim 3 wherein said diffraction grating is on a disc having a center of rotation at said grating center, and said selected axis passes through the center, further comprising means for positioning said light source along said axis and means for sensing said reflections at a position above said source.

5. The apparatus of claim 3 wherein said surface comprises a disc having a spiral track of uniformly and closely spaced groove convolution serving as said diffraction grating.

6. The apparatus of claim 3 wherein said surface comprises a disc having a spiral track of uniformly and closely spaced pits or bumps formed along the convolution of said spiral track, said convolution of pits or bumps serving as said diffraction grating.

7. A method for detecting defects in the topography of a surface having a circular or spiral diffraction grating having a center comprising the steps of:

positioning a substantially point source of polychromatic light along a preselected axis perpendicular to said surface through said center;

illuminating the surface with light from said source;

sensing reflections of diffracted light from said surface by positioning the optical center of the camera lens of a television camera at a predelected position along said axis;

displaying sensed reflections as images on a television monitor; and adjusting the respective illuminating and sensing positions to provide a pattern of diffraction reflections manifesting non-uniform spacing or average surface flatness in said diffraction pattern, wherein defects in the topography appear on the monitor as non-uniformities in the diffraction reflections.

8. Apparatus for detecting defects in the topography of a surface having a circular or spiral diffraction grating having a center comprising:

means for positioning a substantially point source of polychromatic light along a preselected axis perpendicular to said surface through said center;

means for illuminating the surface with light from said source;

means for sensing reflections of diffracted light from said surface by positioning the optical center of the camera lens of a television camera at a preselected position along said axis;

means for displaying sensed reflections as images on a television monitor; and means for adjusting the respective illuminating and sensing positions to provide a pattern of diffraction reflections manifesting non-uniform spacing or average spacing flatness in said diffraction pattern, wherein defects in the topography appear on said monitor as non-uniformities in the diffraction reflections.

* * * * *